United States Patent [19]
Prahl

[11] Patent Number: 5,348,532
[45] Date of Patent: Sep. 20, 1994

[54] ORTHOPEDIC REDRESSMENT SPLINT

[75] Inventor: Jan Prahl, Rullstorf, Fed. Rep. of Germany

[73] Assignee: IPOS GmbH & Co. KG, Lueneburg, Fed. Rep. of Germany

[21] Appl. No.: 832,130

[22] Filed: Feb. 6, 1992

[30] Foreign Application Priority Data

Sep. 24, 1991 [EP] European Pat. Off. ........ 91116200.6

[51] Int. Cl.⁵ .................. A61F 5/00; A43B 7/24
[52] U.S. Cl. .............................. 602/24; 36/142
[58] Field of Search ............. 602/1, 28, 29, 23, 24; 36/140–144, 158, 177, 179

[56] References Cited

U.S. PATENT DOCUMENTS

| | | | |
|---|---|---|---|
| 1,572 | 4/1840 | Brown | 602/29 |
| 1,484,165 | 2/1924 | Wilson | 36/158 |
| 1,491,500 | 4/1924 | Wambaugh | 36/158 |
| 1,804,549 | 5/1931 | Temler | 36/158 |
| 2,269,815 | 1/1942 | Goodman | 36/143 |
| 2,663,294 | 12/1953 | Harrison | 602/28 |
| 2,849,808 | 9/1958 | Coplans | 36/158 |
| 2,967,360 | 1/1961 | Rice | 36/140 |
| 3,424,166 | 1/1969 | Gibbons | 36/142 |
| 4,393,876 | 7/1983 | Dieterich | 36/142 |

FOREIGN PATENT DOCUMENTS 0027762 4/1981 European Pat. Off. .

*Primary Examiner*—Michael A. Brown
*Attorney, Agent, or Firm*—Townsend and Townsend Khourie and Crew

[57] ABSTRACT

Described is an orthopedic redressment splint for correcting the adduction of the forefoot and metatarsus with an anterior half sole enclosing at least laterally the deformed portion of the foot and a posterior half sole (10, 11) which are flexibly and swivelably interconnected through a vertical to the half sole plane defined by means of a pivot pin (13) and which are provided with a spring (17), whose elastic force acts in the lateral direction upon the anterior half sole (10), in which the pivot pin (13) is disposed on the outer edge of the two half soles (10, 11) and the spring is a pressure spring (17) with the aid of which the half soles (10, 11) are pressure-loaded relative to each other on the medial side (FIG. 1).

17 Claims, 2 Drawing Sheets

ORTHOPEDIC REDRESSMENT SPLINT

The present invention relates to an orthopedic redressment splint for correction the adduction of the forefoot and the metatarsus with an anterior half sole enclosing the deformed foot portion at least laterally and a posterior half sole which half soles are flexibly and swivelably interconnected a vertical to the half sole plane defined by means of a pivot pin and which are provided with a spring, whose elastic force acts in the lateral direction upon the anterior half sole.

Said redressment splint, which is also designated as apes adductus splint, is employed especially for the treatment of the congenital or acquired pes adductus in infants. In an early treatment stage one frequently succeeds in bringing the foot into a normal position by means of said splints alone. In the case of serious deformities or in later treatment stages, it is possible to also make use of the pes adductus splint after an operation of the foot in a supportive manner. If the forefoot adduction is part of a club foot deformity which, inter alia, is accompanied with a pronation of the heel bone, the redressment splint has to be connected to a calf guide means and a knee bending fixation means in order to render a treatment of the club foot possible in a promising manner. However, with regard to the construction of the redressment splint, no fundamental difference exists. The deformity of the foot which is amenable to treatment with said redressment splint may consist in the deformation of the first metatarsal which deviates toward medial, while the other four metatarsals proceed normally, or in a medial deviation of all five metatarsal bones, the typical pes adductus.

In the redressment splints known according to the state of the art as are described, inter alia, in the EP 0 027 762, the pivot pin is located on the medial half shell side, while on the opposite side a spiral spring acts upon the two half soles in such a way that the medially deviating foot portions are pressed laterally. The following disadvantages result herefrom. As already mentioned in the foregoing, pes adductus splints are frequently employed with infants whose bones of the foot still are in the growing stage. Due to the pivot pin arrangement on the medial side, this side is unavoidably subjected to a strong compression. Depending on the tension of the spiral spring, the big toe is strongly compressed. Increasing from medial to lateral, a powerful compression of the tarsus is brought about.

That is why it is the object of the present invention to improve the redressment splint described in the beginning in such a way that, with a redesigned splint, a reduced compression exists on the lateral side.

BACKGROUND OF THE INVENTION

This technical problem is solved by the orthopedic redressment splint described in claim 1, whose characteristic feature according to the invention consists in that the pivot is disposed on the external edge of the two half soles, thus laterally, and in that the spring used is a pressure spring which compressively loads the half soles relative to each other on the medial side.

By the dislocation of the swivel joint onto the lateral side, this side is significantly relieved of the compression which, according to the state of the art, existed in the constructions known up until now according to the state of the art. The tarsal bones remain relieved to large extent. At the same time, the position of the point of rotation on the lateral side has a straightening-out effect on the foot.

Further developments of the invention are described in claims 2 through 19.

Thus the pivot pin is preferably located at the level where the condyle of the fifth tarsal bone is articulated. An optimal application of pressure on the forefoot is ensured by this.

For the purpose of a simple construction, the two half soles are each provided on their outside with an extension, in which case the extensions overlap each other and are penetrated by the pivoting pin. In addition, by preference, at a distance from the pivoting pin in the direction of the inner edge, on each of the two half soles, prepared pivotal points for the pressure spring are to be found which are located in particular within the area of the inner edge of the half sole. It is possible, however, for more than two pivotal points to be prepared, for example, in order to displace the spring for constructional reasons from the medial side toward the center. However, in doing this, regard will have to be had that the lever arm is shortened in a corresponding manner.

In principle, no restriction exists with regard to the type of spring used. However, in a further development of the invention, a spiral spring is made use of, whose legs, at the end, lie essentially parallel to the outer edge of the half sole.

According to a further embodiment of the invention, the half soles are in each case provided with an angular section of non-resilient material, the angular sections being in each case swivelably retained at the end by the pivot pin and their free ends being located in the direction of the inner edge and reaching up to the same. These angular sections which may e.g. be comprised of metal, possess in each case prepared pivotal points for the pressure spring. This type of construction has the advantage that especially the shell-shaped foot-pad areas of the half soles may be comprised of a material capable of adapting to the shape of the foot under pressure.

According to a further embodiment of the invention, provision is made for the redressment splint to be constructed in the form of a shoe or boot portion, as is described in principle in the EP 0 027 762.

BRIEF DESCRIPTION OF THE DRAWINGS

Embodiment examples of the invention are depicted in the drawings. Thus.

DESCRIPTION OF THE PREFERRED EMBODIMENT

Figure 1:
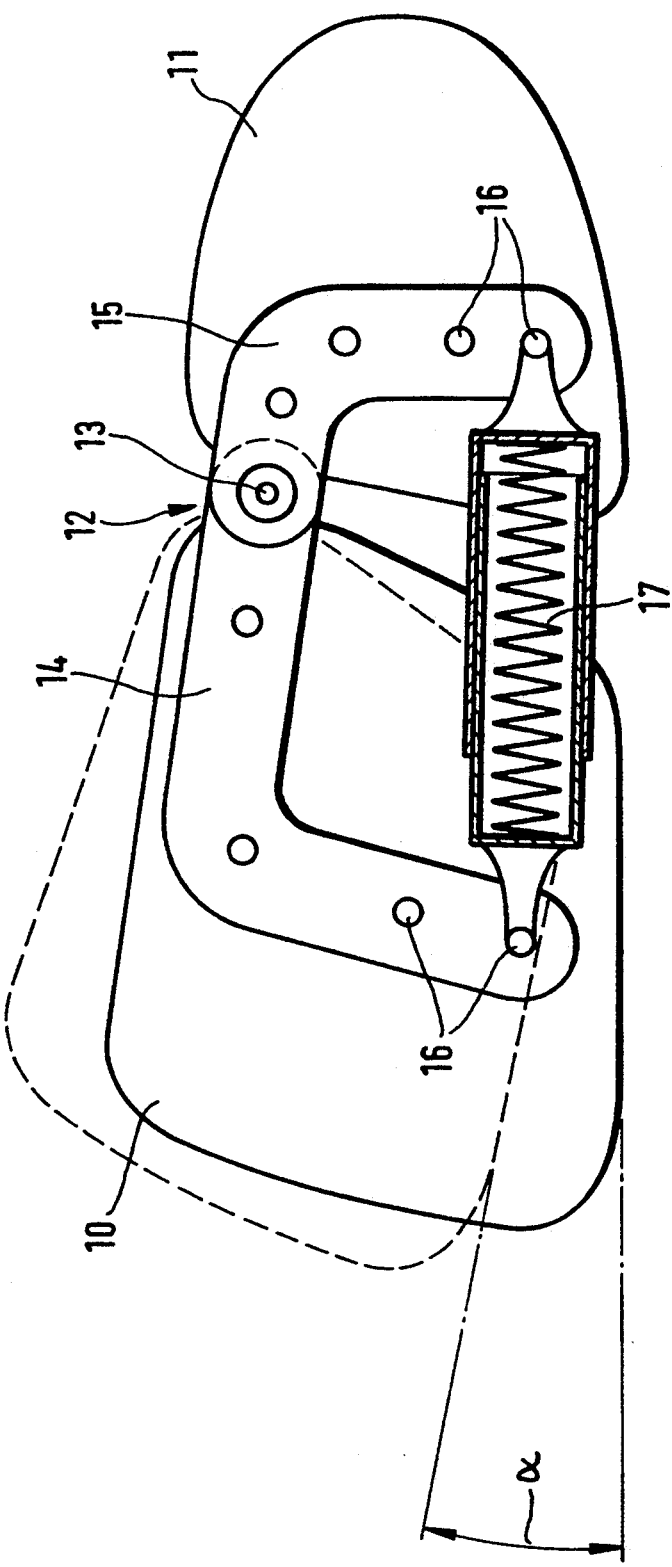
FIGS. 1 and 2 each show in principle representations of redressment splints with different pressure springs.

The redressment splint comprises an anterior half sole 10 and a posterior half sole 11, which are interconnected with the aid of a swivel joint 12. The swivel joint 12 comprises a pivot pin 13 which penetrates respective, mutually overlapping extensions of the anterior and posterior half sole. These extensions form part of respective angular sections 14 and 15 with prepared pivotal points 16 for a pressure spring 17 (FIG. 1) or 18 (FIG. 2).

The invention comprises the construction arrangement of the pivotal point being located on the outer edge, the lateral side, of the half soles 10 and 11. In the non-loaded state, the half soles assume the position depicted with full lines. When subjected to a load, the pressure springs 17 or 18, respectively, the anterior half sole swivels through an angle to the lateral, whereby a pertinent pressure is exerted upon the forefoot.

In the embodiment according to FIG. 1, the elongated pressure spring 17 lies essentially parallel to and within the area of the inner edge of the half soles 10 and 11, while the pressure spring 17 is in each case secured to the free ends of the angular sections 14 and 15.

Figure 2:
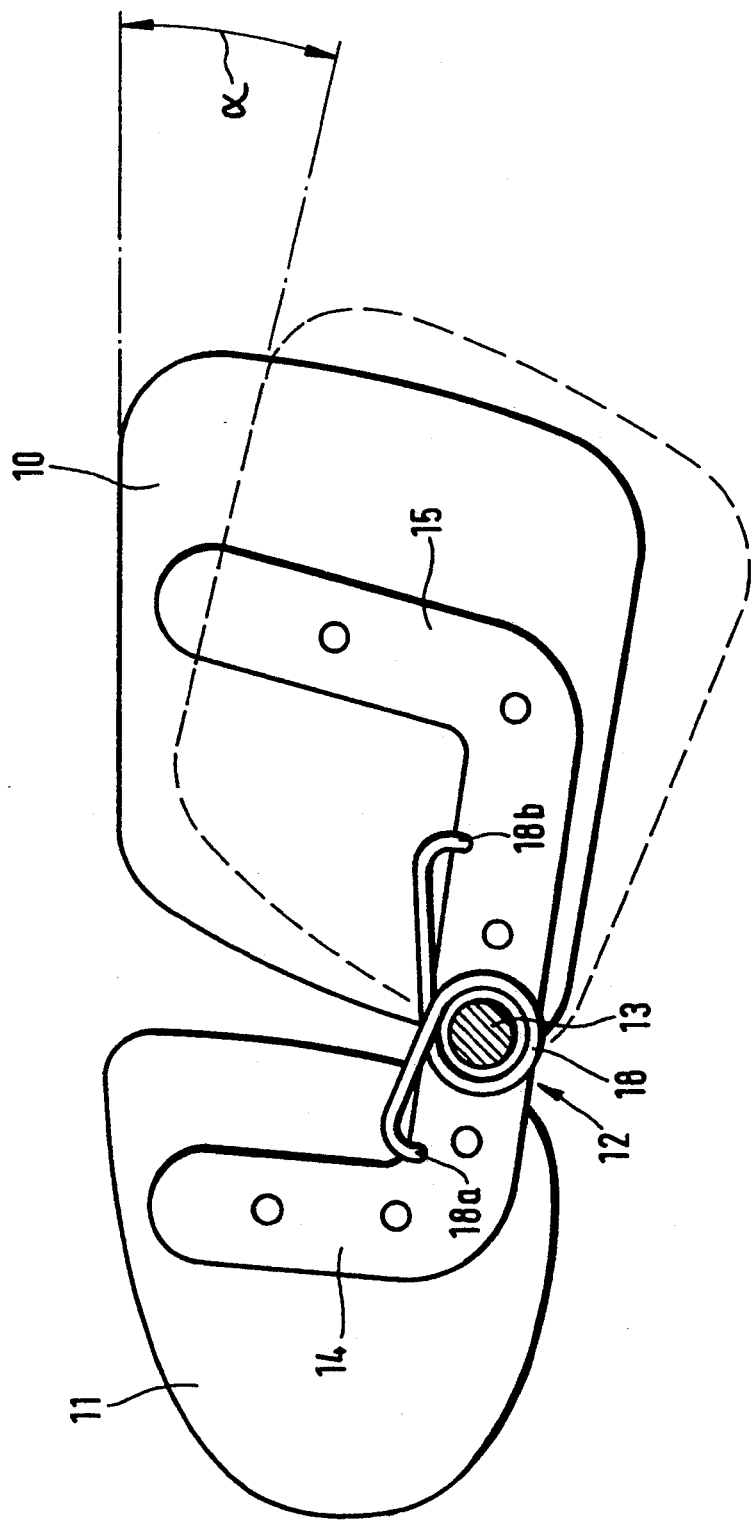

In the embodiment according to FIG. 2, the pressure spring 18 is comprised of a spiral spring whose free resilient ends 18a and 18b act upon the sides of the angular sections 14 and 15 within the lateral area. The remaining part of the pressure spring 18 is disposed medially about the pivot pin 13.

As results from a comparison between the contour of the anterior half sole drawn in full lines and the "swiveled" contour shown in dashed lines, when the springs 17 and 18 exert pressure, the anterior half sole is drawn "toward the front", whereby the foot is more or less pulled lengthwise and a correction of the adduction position is encouraged to a significant degree.

What is claimed is:

1. Orthopedic redressment splint for correcting an adduction of a forefoot and metatarsus comprising:
   an anterior half sole enclosing at least laterally a deformed foot portion;
   a posterior half sole for enclosing at least part of a remaining foot portion;
   pivot means flexibly and swivelably interconnected through a vertical to a half sole plane defined by means of a pivot pin disposed on a lateral edge of the two half soles;
   a spring whose elastic force acts in a lateral direction upon the half soles for spring-loading the half soles relative to each other on a medial side, wherein each of the two half soles has at least one prepared pivotal point adapted for the pressure spring.

2. An orthopedic redressment splint according to claim 1, wherein the pivot pin is located at a level of articulation of a condyle of a fifth metatarsal bone.

3. An orthopedic redressment splint according to claim 1, wherein that the two half soles in each case, on their lateral side have an extension, said extensions overlap each other and are penetrated by the pivot pin.

4. An orthopedic redressment splint according to claim 4, wherein the pivotal points are located within an area of the inner edge of the half soles.

5. An orthopedic redressment splint according to claim 1, wherein the spring is a spiral spring disposed around the pivot pin, having legs which, at their ends, are located essentially parallel to the outer edge of the half soles.

6. An orthopedic redressment splint according to claim 1, wherein the half soles are in each case provided with an angular section of non-resilient material which, in each case, at their ends, are swivelably retained by the pivot pin and whose free end lies in the direction toward the inner edge and reaches up as far as to the same, while these angular sections in each case, are provided with prepared pivotal points for the pressure spring.

7. An orthopedic redressment splint according to claim 1, wherein the splint is constructed in the form of a shoe or a boot portion.

8. An orthopedic redressment splint for correcting an adduction of a forefoot and metatarsus comprising in combination:
   an anterior half sole enclosing at least laterally a deformed foot portion;
   a posterior half sole for enclosing at least a part of a remaining foot portion;
   a pivot pin is disposed on a lateral edge of the two half soles to flexibly and swivelably interconnected through a vertical to a half sole plane, said pivot pin located at a level of articulation of a Condyle of a fifth metatarsal bone; and,
   a first and second extensions, said extension protruding from the lateral edge of each sole half and overlapping each other and are penetrated by said pivot pin; and,
   a compression spring whose elastic force acts in a lateral direction upon the anterior half sole to load the half soles with a spring bias away from each other on a medial side.

9. An orthopedic redressment splint according to claim 8, wherein the pivotal points are located within an area of the inner edge of the half soles.

10. An orthopedic redressment splint according to claim 8, wherein the spring is a spiral spring disposed around the pivot pin, having legs which, at their ends, are located essentially parallel to the outer edge of the half soles.

11. An orthopedic redressment splint according to claim 8 wherein the half soles are in each case provided with an angular section of non-resilient material which, in each case, at their ends, are swivelably retained by the pivot pin and whose free end lies in the direction toward the inner edge and reaches up as far as to the same, while these angular sections in each case, are provided with prepared pivotal points for the pressure spring.

12. An orthopedic redressment splint according to claim 8, wherein the splint is constructed in the form of a shoe or a boot portion.

13. A method for correcting an adduction of a forefoot and metatarsus comprising:
   providing an orthopedic redressment splint having an anterior half sole for enclosing at least laterally a deformed foot portion and a posterior half sole;
   providing a pivot pin disposed on a lateral edge of the two half soles to flexibly and swivelably interconnected through a vertical to a half sole plane;
   providing a spring whose elastic force acts in a lateral direction upon the anterior half sole in that the spring is a pressure spring with the aid of which the half soles are spring-loaded relative to each other on a medial side; and,
   placing a foot within said splint.

14. The method of claim 13 further comprising selecting a redressment splint having the pivot pin placing the pivot pin at a level of articulation of a condyle of a fifth metatarsal bone and having the two half soles in each case, on their outside, including an extension, said extensions overlapping each other and penetrated by the pivot pin.

15. A method of manufacture of an orthopedic redressment splint for correcting an adduction of a forefoot and metatarsus comprising:
   forming an anterior half sole adapted to enclose at least laterally a deformed foot portion and a posterior half sole;
   placing a pivot pin between said sole halves on the lateral edge of said sole halves to flexibly and swivelably interconnected through a vertical;

providing a spring whose elastic force acts in a lateral direction upon the anterior half sole characterized in that the pivot pin is disposed on a lateral edge of the two half soles and in that the spring is a pressure spring with the aid of which the half soles are spring-loaded relative to each other on a medial side.

16. The method of claim 15 further comprising positioning the pivot pin such that in use the pivot pin is at a level of articulation of a condyle of a fifth metatarsal bone.

17. The method of claim 15 further comprising providing the two half soles in each case, on their outside, with an extension, said extensions overlapping each other and penetrated by the pivot pin.

* * * * *